United States Patent [19]

Maier et al.

[11] 4,451,284
[45] May 29, 1984

[54] DERIVATIVES OF 2-NITRO-4- OR -5-PYRIDYLOXYPHENYLPHOSPHONIC ACID, THE PREPARATION THEREOF, THE USE THEREOF AS HERBICIDES AND/OR PLANT GROWTH REGULATORS

[75] Inventors: Ludwig Maier, Arlesheim; Hermann Rempfler, Ettingen; Dieter Dürr, Bottmingen, all of Switzerland

[73] Assignee: Ciba-Geigy Corporation, Ardsley, N.Y.

0

[21] Appl. No.: 399,504

[22] Filed: Jul. 19, 1982

[30] Foreign Application Priority Data

Jul. 28, 1981 [CH] Switzerland ................. 4891/81

[51] Int. Cl.³ .............. C07F 9/58; A01N 43/40; A61K 31/44
[52] U.S. Cl. .............................. 71/94; 546/22; 424/200; 424/263
[58] Field of Search ............. 546/22; 71/94; 424/263, 424/200

[56] References Cited

U.S. PATENT DOCUMENTS 4,322,375 3/1982 Maier et al. ................. 260/951
4,326,880 4/1982 Rempfler ..................... 71/94

FOREIGN PATENT DOCUMENTS 176 1/1979 European Pat. Off. ........... 568/585
7471 2/1980 European Pat. Off. ........... 546/301

OTHER PUBLICATIONS

Maier et al., Chemical Abstracts, vol. 99, No. 5, Abst. No. 38,638W, Aug. 1, 1983.

*Primary Examiner*—Alan L. Rotman
*Attorney, Agent, or Firm*—Frederick H. Rabin

[57] ABSTRACT

The invention relates to novel 2-nitro-4- or -5-pyridyloxyphenylphosphonic acid derivatives of the formula

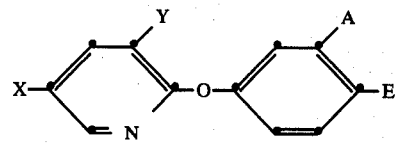

wherein X is halogen or trifluoromethyl, Y is hydrogen or halogen, one of the two substituents A and E is a phosphonate group

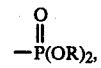

wherein R is $C_1$–$C_4$ alkyl or hydrogen, and the other is a nitro group, including the metal salts thereof and the salts thereof with ammonium and organic nitrogen bases, and to the preparation and use thereof. These compounds may be used for controlling weeds, regulating plant growth, or as microbicides.

62 Claims, No Drawings

DERIVATIVES OF 2-NITRO-4- OR -5-PYRIDYLOXYPHENYLPHOSPHONIC ACID, THE PREPARATION THEREOF, THE USE THEREOF AS HERBICIDES AND/OR PLANT GROWTH REGULATORS

The present invention relates to novel 2-nitro-4- or -5-pyridyloxyphenylphosphonic acid derivatives of the formula I, to the preparation of these compounds, to plant growth regulating and/or herbicidal and/or microbicidal compositions which contain a compound of the formula I as active ingredient, and to a method of regulating plant growth, of controlling weeds and/or of controlling phytopathogenic microorganisms, which comprises the use of compounds of the formula I.

The invention relates further to novel intermediates of the formula II employed for obtaining compounds of the formula I, to the preparation of said intermediates, to herbicidal compositions which contain a compound of the formula II as active ingredient, and to a method of controlling weeds which comprises the use of compounds of the formula II.

2-Substituted 5-phenoxyphenylphosphonic acid derivatives having herbicidal and growth regulating properties are described in European patent application No. 14684. Pyridyloxyphenoxyalkanecarboxylic acid derivatives having herbicidal and growth regulating properties are known from European patent application No. 176. Further, 2-substituted phenoxy-3-chloro-5-trifluoromethylpyridines having herbicidal properties are disclosed in U.S. Pat. No. 4,235,621. Finally, 5-(pyridyl-2'-oxy)-2-nitrobenzoic acid derivatives having herbicidal properties are known from European patent application No. 24259.

The 2-nitro-4- or -5-pyridyloxyphenylphosphonic acid derivatives of this invention have the formula I

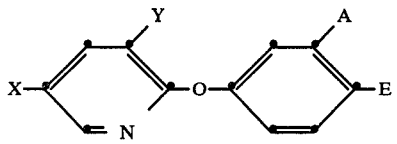

wherein X is halogen or trifluoromethyl, Y is hydrogen or halogen, one of the two substituents A and E is a phosphonate group

wherein R is $C_1$–$C_4$alkyl or hydrogen, and the other is a nitro group, including the metal salts thereof and the salts thereof with ammonium and organic nitrogen bases.

Accordingly, the compounds of formula I comprise free acids, esters and salts.

In the definition of formula (I) above, halogen denotes fluorine, bromine, iodine and, in particular, chlorine. $C_1$–$C_4$Alkyl may be methyl, ethyl, n-propyl, isopropyl, primary, secondary and tertiary butyl and isobutyl, with methyl and ethyl being preferred.

Metals suitable for salt formation are alkaline earth metals such as magnesium or calcium, and especially alkali metals such as lithium, potassium and, preferably, sodium. Suitable salt formers are also transition metals, e.g. iron, nickel, cobalt, copper, zinc, chromium or manganese. Examples of organic nitrogen bases which are suitable for salt formation are primary, secondary and tertiary aliphatic and aromatic amines which may be hydroxylated at the hydrocarbon radical, e.g. methylamine, ethylamine, propylamine, isopropylamine, the four isomeric butylamines, dimethylamine, diethylamine, dipropylamine, diisopropylamine, di-n-butylamine, pyrrolidine, piperidine, morpholine, trimethylamine, triethylamine, tripropylamine, quinuclidine, pyridine, quinoline, isoquinoline, as well as methanolamine, ethanolamine, propanolamine, dimethanolamine, diethanolamine, or triethanolamine. Quaternary ammonium bases may also be used as organic nitrogen bases.

Examples of quaternary ammonium bases are the ammonium cation, tetraalkylammonium cations in which the alkyl moieties independently of one another are straight chain or branched $C_1$–$C_6$alkyl groups, e.g. the tetramethylammonium cation, the tetraethylammonium cation or the trimethylethylammonium cation, as well as the trimethylbenzylammonium cation, the triethylbenzylammonium cation and the trimethyl-2-hydroxyethylammonium cation.

Preferred compounds of formula I are those in which X is chlorine or trifluoromethyl, Y is hydrogen or chlorine, one of A and E is the phosphonate group

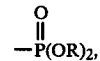

wherein R is hydrogen, methyl or ethyl, and the other is the nitro group.

Particularly interesting compounds of formula I are those in which A is the phosphonate group

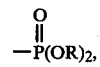

wherein R is hydrogen, methyl or ethyl, E is the nitro group, and X and Y are as defined for formula I.

The most preferred compounds of formula I are those in which A is the phosphonate group

wherein R is hydrogen, methyl or ethyl, E is the nitro group, X is chlorine or trifluoromethyl and Y is hydrogen or chlorine.

Particularly preferred compounds are: dimethyl 2-nitro-5-(5'-trifluoromethyl-2'-pyridyloxy)phenylphosphonate, 2-nitro-5-(5'-trifluoromethyl-2'-pyridyloxy)-phenylphosphonic acid, dimethyl 2-nitro-5-(3',5'-dichloro-2'-pyridyloxy)phenylphosphonate, 2-nitro-5-(3',5'-dichloro-2'-pyridyloxy)phenylphosphonic acid, dimethyl 2-nitro-5-(3'-chloro-5'-trifluoromethyl-2'-pyridyloxy)phenylphosphonate, diethyl 2-nitro-5-(3'-chloro-5'-trifluoromethyl-2'-pyridyloxy)phenylphosphonate, 2-nitro-5-(3'-chloro-5'-trifluoromethyl-2'-pyridyloxy)phenylphosphonic acid, diethyl 2-nitro-5-(3',5'-dichloro-2'-pyridyloxy)phenylphosphonate, diethyl 2-nitro-5-(5'-trifluoromethyl-2'-pyridyloxy)-phenylphosphonate, and dimethyl 2-nitro-4-(5'-trifluoromethyl-2'-pyridyloxy)phenylphosphonate.

The preparation of the novel phosphonic acid derivatives of formula I is carried out in similar manner to the known method of obtaining 2-nitrophenylphosphonic acids (J. Chem. Soc. (C), 1969, 1314) by reacting a 1,2-dinitro-4-pyridyloxybenzene of the formula II

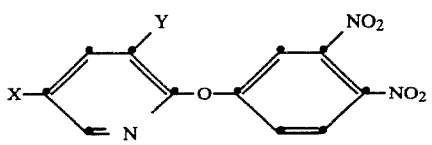

wherein X is halogen or trifluoromethyl and Y is hydrogen or halogen, with a trialkylphosphite of the formula III $P(OR')_3$ (III)

wherein R' is $C_1$-$C_4$alkyl, and, if desired, converting the resultant dialkyl phosphonate of the formula IV

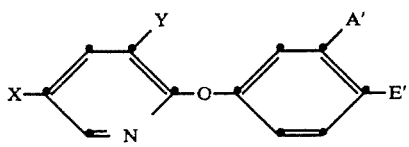

wherein X and Y are as defined for formula II, one of the two substituents A' and E' is a phosphonate group

wherein R' is as defined above, and the other is a nitro group, in a manner which is known per se, into the corresponding free phosphonic acid, a metal salt or a salt with ammonium or with an organic nitrogen base.

The reaction of a compound of the formula II with a compound of the formula III is conveniently carried out at a temperature in the range from 50° to 150° C., preferably from 70° to 120° C. The reaction can be carried out without a solvent; but the use of an organic aprotic solvent, e.g. acetonitrile, benzene or toluene, is preferred.

The phosphonate ester group can be readily converted into the phosphonic acid dichloride e.g. by treatment with 2 moles of $SOCl_2$ in the presence of dimethyl formamide as catalyst, at elevated temperature, in accordance with the method described in U.S. Pat. No. 4,213,922. The dichloride can be converted by hydrolysis into the free phosphonic acid.

The free phosphonic acid can also be prepared by treating the dialkyl phosphonate with concentrated hydrochloric acid or by reacting it with $(CH_3)_3SiBr$, and hydrolysing the resultant silyl compound.

The intermediates of formula II

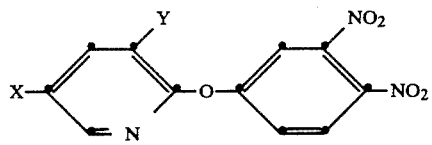

wherein X is halogen or trifluoromethyl and Y is hydrogen or halogen, which have been specially developed for obtaining the compounds of formula I, are novel and likewise constitute an object of the invention.

The compounds of formula II are prepared by nitrating a compound of the formula V

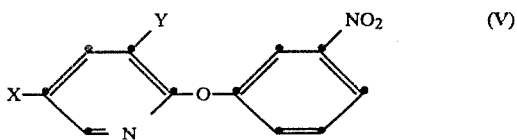

wherein X is halogen or trifluoromethyl and Y is hydrogen or halogen, with a nitrating acid mixture. Conventional mixtures, e.g. of concentrated sulfuric acid and alkali nitrate salts, may be employed as nitrating acid mixture. The nitration is exothermic and is conveniently carried out under normal pressure with cooling or at most at room temperature.

The starting materials of formula V can be prepared in similar manner to that of the known method of preparing 3-nitrodiphenyl ethers (European patent application No. 7471) by reacting a compound of the formula VI

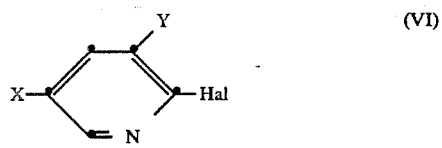

wherein X is halogen or trifluoromethyl, Y is hydrogen or halogen and Hal is halogen, in the presence of a base and preferably in an inert organic solvent, with meta-nitrophenol. The reaction may be carried out without or in the presence of a solvent or diluent which is inert to the reactants. It is preferred to use a polar organic solvent such as methyl ethyl ketone, dimethyl formamide or dimethyl sulfoxide. The reaction temperatures are in the range from 0° to 200° C., preferably from 20° to 100° C., and the reaction time is from about one hour to several days, depending on the starting material, chosen reaction temperature and solvent. The reaction is usually carried out under normal pressure. Suitable bases are inorganic or organic bases, e.g. KOH, $NaOCH_3$, $NaHCO_3$, $K_2CO_3$, potassium tert-butylate or triethylamine.

The starting materials of formula VI are known or they may be prepared by methods similar to known ones.

For application as herbicides, growth regulators or microbicides, the compounds of formula I are used in unmodified form or, preferably, together with the adjuvants conventionally employed in the art of formulation, and are therefore formulated in known manner to e.g. emulsifiable concentrates, brushable pastes, directly sprayable or dilutable solutions, dilute emulsions, wettable powders, soluble powders, dusts, granulates, and also encapsulations in e.g. polymer substances. Like the nature of the compositions, the methods of application, such as spraying, atomising, dusting, scattering or pouring, are chosen in accordance with the intended objectives and the prevailing circumstances.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalates or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyl taurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ioic surfactants are the water-soluble adducts of polyethylene oxide with polypropylene glycol, ethylenediamine polypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan are also suitable non-ionic surfactants, e.g. polyoxyethylene sorbitan trioleate.

Cationic surfactants are preferably quaternary ammonium salts which contain, as N-substituent, at least one $C_8$–$C_{22}$-alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ringwood, N.J., 1980, and Sisely and Wood, "Encyclopedia of Surface Active Agents", Chemical Publishing Co., Inc. New York, 1980.

The agrochemical compositions usually contain 0.1 to 99%, preferably 0.1 to 95%, of a compound of the formula I, 1 to 99.9%, preferably 99.8 to 5%, of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients, such as stabilisers, antifoams, viscosity regulators, binders, tackifiers as well as fertilisers or other active ingredients in order to obtain special effects.

The particulars specified above relating to formulations and their use, as well as the formulation examples which follow, also apply to compounds of formula II.

The compounds of formulae I and II have herbicidal properties and are suitable for the pre- and postemergence control of monocot and dicot weeds.

The compounds of formula I additionally have growth regulating properties. Experience made so far with the application of growth regulators has shown that the compounds are able to influence the plants so as to bring about one or more different responses. These responses are largely dependent on the time of application, i.e. on the physiological state of the seed or on the development stage of the plant, on the nature of the application as well as, in particular, on the concentration employed. Such responses differ in turn, depending on the species of plant. The application of compounds of the formula I thus affords the possibility of influencing plant growth in the desired manner.

For example, plant growth can be regulated with the compounds of formula I so as to stimulate generative growth and thereby to bring about an increase in yield. Cultivated plants the yield of which can be substantially increased are, in particular, leguminosae such as beans, peas, lentils and, most particularly, soya beans. The increase in yield can take the form of an increase in the number of pods and/or in their weight.

Further, the novel compounds of formula I also stimulate the root growth of cultivated plants, especially of cotton plants and cereals, most particularly of wheat. This results in a better supply of water and nutrients to the plants and gives increased protection against the lodging of cereal crops as a consequence of gales or thunderstorms.

The compounds of formula I also have microbicidal properties and are suitable for controlling phytopathogenic fungi or bacteria.

PREPARATION OF INTERMEDIATES OF THE FORMULA II

EXAMPLE 1

1,2-dinitro-4-(3',5'-dichloro-2'-pyridyloxy)benzene (compound II-1)

25 g of 3-(3',5'-dichloro-2'-pyridyloxy)nitrobenzene are added to 100 ml of concentrated sulfuric acid and 25 ml of ethylene chloride. A solution of 5.7 g of fuming nitric acid in 8.8 g of concentrated sulfuric acid is added dropwise at 10°–15° C. over 30 minutes. The reaction mixture is then stirred for 2 hours at room temperature and poured onto ice. The crystalline precipitate is isolated by filtration, washed with water and recrystallised from alcohol. Yield: 18.5 g of 1,2-dinitro-4-(3',5'-dichloro-2'-pyridyloxy)benzene with a melting point of 163°–165° C.

The following compounds of formula II may also be prepared in analogous manner:

TABLE 1

| Compound | X | Y | m.p. |
| --- | --- | --- | --- |
| II-2 | $CF_3$ | Cl | 95–98° C. |
| II-3 | $CF_3$ | H | 82–85° C. |

PREPARATORY EXAMPLES FOR COMPOUNDS OF FORMULA I

EXAMPLE 2

Dimethyl 2-nitro-5-(5'-trifluoromethyl-2'-pyridyloxy)phenylphosphonate (compound 1)

With stirring, a mixture of 24.8 g of 1,2-dinitro-4-(5'-trifluoromethyl-2'-pyridyloxy)benzene and 10.7 ml of trimethylphosphite in 100 ml of toluene is heated to reflux until no more methyl nitrite is formed (about 40 hours). The dark solution is concentrated in a rotary evaporator and the residue is chromatographed over silica gel using ethyl acetate as eluant, affording initially 8 g (27.1% of theory) of the title compound in the form of an orange oil; $n_D^{20}=1.5315$.

Analysis of the final product $C_{14}H_{12}F_3N_2O_6P$ (393.2): Calculated: C 42.87, H 3.09, N 7.14, F 14.53%. Found: C 41.50, H 3.23, N 6.86, F 14.11%. $^1$H-NMR (in CDCl$_3$): OCH$_3$ 3.9 ppm ($J_{POCH}=11$ Hz, 6 H); aromat. CH from 7.15–8.6 (m, 6H).

A further fraction consists of 1.5 g (5.1% of theory) of dimethyl 2-nitro-4-(5'-trifluoromethyl-2'-pyridyloxy)phenylphosphonate in the form of an orange oil (compound 2). $^1$H-NMR (in CDCl$_3$) shows at 8.1 ppm a proton which couples with another proton and additionally shows a $J_{PCH}=13-14$ Hz. Diethyl 2-nitro-5-(5'-trifluoromethyl-2'-pyridyloxy)phenylphosphonate (compound 10) with a melting point of 75°–76° C. is obtained in analogous manner.

EXAMPLE 3

2-Nitro-5-(5'-trifluoromethyl-2'-pyridyloxy)phenylphosphonic acid (compound 3)

A mixture of 7 g of dimethyl 2-nitro-5-(5'-trifluoromethyl-2'-pyridyloxy)phenylphosphonate and 6 ml of (CH$_3$)$_3$SiBr is kept for 2 days at room temperature, then poured into ethanol and concentrated in a rotary evaporator. The residue is dissolved in ethanol (50 ml) and 2-nitro-5-(5'-trifluoromethyl-2'-pyridyloxy)phenylphosphonic acid is precipitated by adding 100 ml of water. The crystalline product (3.8 g=58.6% of theory) is isolated by filtration and dried in vacuo at 80° C. Melting point: 217°–219° C. (black melt).

Analysis of the final product $C_{12}H_8F_3N_2O_6P$ (364.1): Calculated: C 39.58, H 2.22, N 7.69, F 15.65%. Found: C 39.64, H 2.31, N 7.81, F 15.64%. $^1$H-NMR (in CD$_3$OD): OH 5.2 ppm (s, 2H); aromat. H 7.2–8.7 (m, 6H).

EXAMPLE 4

Dimethyl 2-nitro-5-(3',5'-dichloro-2'-pyridyloxy)phenylphosphonate (compound 4)

With stirring, a mixture of 26.9 g of 1,2-dinitro-4-(3',5'-dichloro-2'-pyridyloxy)benzene, 11.5 ml of trimethylphosphite and 100 ml of toluene is heated to reflux for 48 hours. The reaction mixture is concentrated and the residue is chromatographed over silica gel (Hesh 60) with ethyl acetate as eluant. The eluate is concentrated and the residue is recrystallised from methylene chloride/diisopropyl ether. Yield: 10.3 g (32.2% of theory) of dimethyl 2-nitro-5-(3',5'-dichloro-2'-pyridyloxy)phenylphosphonate in the form of yellow crystals with a melting point of 101°–103° C.

Analysis of the final product $C_{13}H_{11}Cl_2N_2O_6P$ (393.1): Calculated: C 39.72, H 2.82, N 7.13, Cl 18.04%. Found: C 39.87, H 2.94, N 7.18, Cl 17.96%. $^1$H-NMR (in CDCl$_3$): OCH$_3$ 3.9 ppm (d, $J_{POCH}=11$ Hz, 6H); aromat. H 7.3–8.3 ppm (5H).

Diethyl 2-nitro-5-(3',5'-dichloro-2'-pyridyloxy)phenylphosphonate is obtained in analogous manner in the form of a brown viscous oil (compound 9).

EXAMPLE 5

2-Nitro-5-(3',5'-dichloro-2'-pyridyloxy)phenylphosphonic acid (compound 5)

A mixture of 6.15 g of dimethyl 2-nitro-5-(3',5'-dichloro-2'-pyridyloxy)phosphonate and 10 ml of (CH$_3$)$_3$SiBr is stirred for 20 hours at room temperature. Then alcohol is added and the mixture is concentrated in a rotary evaporator, affording 4.9 g of 2-nitro-5-(3',5'-dichloro-2'-pyridyloxy)phenylphosphonic acid in the form of orange crystals with a melting point of 238° C. (decompos.)

Analysis of the final product $C_{11}H_7Cl_2N_2O_6P$ (365.0): Calculated: C 36.19, H 1.93, N 7.67, Cl 19.42%. Found: C 34.92, H 1.97, N 7.36, Cl 19.36%. $^1$H-NMR (in $CD_3OD/D_2O$): OH 5.1 ppm (br., 2H); aromat. H 7.2–8.6 ppm (br., 5H).

EXAMPLE 6

Dimethyl 2-nitro-5-(3'-chloro-5'-trifluoromethyl-2'-pyridyloxy)-phenylphosphonate (compound 6)

With stirring, a mixture of 10 g of 1,2-dinitro-4-(3'-chloro-5'-trifluoromethyl-2'-pyridyloxy)benzene, 6.4 ml of trimethylphosphite and 35 ml of toluene is heated for 18 hours to reflux, treated with activated carbon and concentrated. The residual yellow oil is purified by chromatography over silica gel with ethyl acetate as eluant, to give 4.42 g (38.3% of theory) of dimethyl 2-nitro-5-(3'-chloro-5'-trifluoromethyl-2'-pyridyloxy)-phenylphosphonate in the form of yellowish crystals with a melting point of 99°–100° C.

Analysis of the final product $C_{14}H_{11}ClF_3N_2O_6P$ (426.6): Calculated: C 39.41, H 2.60, N 6.57%. Found: C 39.33, H 2.69, N 6.46%. $^1$H-NMR (in $CDCl_3$): $OCH_3$ 3.9 ppm (d, $J_{POCH}$=11 Hz, 6H); aromat. H 7.5–8.4 ppm (m, 5H).

EXAMPLE 7

Diethyl 2-nitro-5-(3'-chloro-5'-trifluoromethyl-2'-pyridyloxy)-phenylphosphonate (compound 7)

A mixture of 10 g of 1,2-dinitro-4-(3'-chloro-5'-trifluoromethyl-2'-pyridyloxy)benzene, 8.6 ml of triethylphosphite and 35 ml of toluene is heated to reflux for 16 hours in accordance with the method described in Example 6. Purification of the crude product by chromatography yields 7.8 g (63.5% of theory) of diethyl 2-nitro-5-(3'-chloro-5'-trifluoromethyl-2'-pyridyloxy)-phenylphosphonate in the form of a highly viscous oil.

Analysis of the final product $C_{16}H_{15}ClF_3N_2O_6P$ (454.7): Calculated: C 42.26, H 3.32, N 6.16, Cl 7.80, P 6.81%. Found: C 42.25, H 3.52, N 6.17, Cl 7.89, P 6.61%. $^1$H-NMR (in $CDCl_3$): $CH_3$ 1.37 ppm (t, 6H); $OCH_2$ 4.2 ppm (qui, 4H); aromat. H 7.35–8.4 (m, 5H).

EXAMPLE 8

2-Nitro-5-(3'-chloro-5'-trifluoromethyl-2'-pyridyloxy)-phenylphosphonic acid (compound 8)

A mixture of 3.5 g of diethyl 2-nitro-5-(3'-chloro-5'-trifluoromethyl-2'-pyridyloxy)phenylphosphonate and 50 ml of 20% HCl is heated to reflux for 14 hours and then concentrated in a rotary evaporator. Yield: 2.54 g (82.7% of theory) of 2-nitro-5-(3'-chloro-5'-trifluoromethyl-2'-pyridyloxy)phenylphosphonic acid with a melting point of 156°–159° C. $^1$H-NMR (in $D_2O/NaOD$): OH 4.75 (s, 2H); aromat. H 6.2–8.1 (m, 5H).

Formulation Examples for liquid active ingredients of the formula I or II (throughout, percentages are by weight)

| 9. Emulsifiable concentrates | (a) | (b) | (c) |
|---|---|---|---|
| Compound of Examples 1–8 or Table 1 | 25% | 40% | 50% |
| calcium dodecylbenzenesulfonate | 5% | 8% | 6% |
| castor oil polyethylene glycol ether (36 moles of ethylene oxide) | 5% | — | — |

-continued

| 9. Emulsifiable concentrates | (a) | (b) | (c) |
|---|---|---|---|
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 10. Solutions | (a) | (b) | (c) | (d) |
|---|---|---|---|---|
| Compound of Examples 1–8 or Table 1 | 80% | 10% | 5% | 95% |
| ethylene glycol monomethyl ether | 20% | — | — | — |
| polyethylene glycol MG 400 | — | 70% | — | — |
| N—methyl-2-pyrrolidone | — | 20% | — | — |
| epoxidised coconut oil | — | — | 1% | 5% |
| ligroin (boiling range 160–190°) | — | — | 94% | — |

These solutions are suitable for application in the form of microdrops.

| 11. Granulates | (a) | (b) |
|---|---|---|
| Compound of Examples 1–8 or Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 12. Dusts | (a) | (b) |
|---|---|---|
| Compound of Examples 1–8 or Table 1 | 2% | 5% |
| highly dispersed silicic acid | 1% | 5% |
| talcum | 97% | — |
| kaolin | — | 90% |

Ready for use dusts are obtained by intimately mixing the carriers with the active ingredient.

Formulation examples for solid active ingredients of the formula I or II (throughout, percentages are by weight)

| 13. Wettable powders | (a) | (b) | (c) |
|---|---|---|---|
| Compound of Examples 1–8 or Table 1 | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 14. Emulsifiable concentrate | |
|---|---|
| Compound of Examples 1–8 or Table 1 | 10% |
| octylphenol polyethylene glycol ether (4–5 moles of ethylene oxide) | 3% |

-continued

| 14. Emulsifiable concentrate | |
|---|---|
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 15. Dusts | (a) | (b) |
|---|---|---|
| Compound of Examples 1-8 or Table 1 | 5% | 8% |
| talcum | 95% | — |
| kaolin | — | 92% |

Ready for use dusts are obtained by mixing the active ingredient with the carriers, and grinding the mixture in a suitable mill.

| 16. Extruder granulate | |
|---|---|
| Compound of Examples 1-8 or Table 1 | 10% |
| sodium lignosulfonate | 2% |
| carboxymethylcellulose | 1% |
| kaolin | 87%. |

The active ingredient is mixed and ground with the adjuvants, and the mixture is subsequently moistened with water. The mixture is extruded and then dried in a stream of air.

| 17. Coated granulate | |
|---|---|
| Compound of Examples 1-8 or Table 1 | 3% |
| polyethylene glycol MG 200 | 3% |
| kaolin | 94% |

The finely ground active ingredient is uniformly applied, in a mixer, to the kaolin moistened with polyethylene glycol. Non-dusty coated granulates are obtained in this manner.

| 18. Suspension concentrate | |
|---|---|
| Compound of Examples 1-8 or Table 1 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32%. |

The finely ground active ingredient is intimately mixed with the adjuvants, giving a suspension concentrate from which suspensions of any desired concentration can be obtained by dilution with water.

BIOLOGICAL EXAMPLES

Example 19

Preemergence herbicidal action (inhibition of germination)

In a greenhouse, immediately after sowing seeds of test plants in seed dishes, the surface of the soil is treated with an aqueous dispersion prepared from a 10% wettable powder formulation of test compounds of formula I. Concentrations of 4 kg of active ingredient per hectare are used. The seed dishes are kept in the greenhouse at 22°–25° C. and 50–70% relative humidity, and the test is evaluated after 3 weeks in accordance with the following rating:

1 = plants have not germinated or have completely died off
2–3 = very pronounced action
4–6 = medium action
7–8 = slight action
9 = no action (as untreated controls)

Of the compounds of formula I, dimethyl 2-nitro-5-(3'-chloro-5'-trifluoromethyl-2'-pyridyloxy)phenylphosphonate (compound 6) in particular is very effective in this test against the weeds Setaria and Stellaria (rating 1) and Sinapis (rating 2).

Example 20

Postemergence herbicidal action (contact herbicide)

The weeds to be tested are sprayed postemergence (in the 4- to 6-leaf stage) with an aqueous dispersion prepared from compounds of formula I formulated as (a) a 10% or (b) a 25% wettable powder or (c) a 25% emulsifiable concentrate, at a rate of application of 4 kg a.i./ha. The plants are kept at 24°–26° C. and 45–60% relative humidity. The test is evaluated 15 days later in accordance with the same rating as used in the preemergence test (Example 19).

Of the compounds of formula I, in particular dimethyl 2-nitro-5-(3'-chloro-5'-trifluoromethyl-2'-pyridyloxy)phenylphosphonate (compound 6), dimethyl 2-nitro-5-(3',5'-dichloro-2'-pyridyloxy)phenylphosphonate (compound 4), dimethyl 2-nitro-5-(5'-trifluoromethyl-2'-pyridyloxy)phenylphosphonate (compound 1), diethyl 2-nitro-5-(3'-chloro-5'-trifluoromethyl-2'-pyridyloxy)phenylphosphonate (compound 7) and diethyl 2-nitro-5-(3',5'-dichloro-2'-pyridyloxy)phenylphosphonate (compound 9), are very effective.

TABLE 2

| Compound | Formulation | Test plant | | |
|---|---|---|---|---|
| | | Solanum | Sinapis | Setaria |
| 6 | (a) | 1 | 1 | 3 |
| 4 | (b) | 2 | 3 | 3 |
| 1 | (c) | 4 | 3 | 4 |
| 7 | (c) | 1 | 2 | 3 |
| 9 | (c) | 1 | 2 | 2 |

Example 21

Regulation of the growth of soya bean plants (a) Soya beans of the "Hark" variety are sown in plastic containers in a mixture of earth/peat/sand (6:3:1). The containers are put into a climatic chamber and the plants develop to the 5–6 trefoil leaf stage after about 5 weeks by optimum control of temperature, light, fertilisation and watering. The plants are then sprayed until wet at rates of application of 0.1, 0.5 and 1.5 kg a.i./ha with the aqueous spray mixture prepared from a compound of formula I formulated as a 25% emulsifiable concentrate. Evaluation is made about 5 weeks after application by comparing the average growth in height and the yield of harvested pods with those of untreated controls (=100%). Of the compounds of formula I, dimethyl 2-nitro-5-(5'-trifluoromethyl-2'-pyridyloxy)phenylphosphonate (compound 1) in particular is very effective.

(b) Under the same test conditions as in (a), but using rates of application of 0.08 to 4 a.i./ha, the following results are obtained e.g. with 2-nitro-5-(5'-trifluoromethyl-2'-pyridyloxy)phenylphosphonic acid (compound 3):

TABLE 3

| kg a.i./ha | 0.08 | 0.40 | 0.80 | 4.00 |
|---|---|---|---|---|
| no. of pods as % of controls | 107 | 119 | 109 | 98 |
| Weight of pods as % of controls | 119 | 119 | 135 | 108 |

(controls = 100%)

Example 22

Stimulation of root growth in wheat

Compounds of formula I are applied in the form of aqueous dispersions prepared from a 25% wettable powder. The test is carried out with seeds which are sown in plastic cylinders measuring 5×30 cm and filled with soil (10 seeds per cylinder). The seeds are (a) treated before sowing at rates of application of 4–130 mg per kg of seeds or (b) are untreated and the soil is sprayed with a dispersion of the active ingredient at rates of application of 0.3 to 3 kg/ha. The cylinders are kept under controlled conditions in a climatic chamber. After 10 days, the seedlings are carefully washed with water to remove the soil and the length and dry weight of the roots are assessed.

Of the compounds of formula I, 2-nitro-5-(5'-trifluoromethyl-2'-pyridyloxy)phenylphosphonic acid (compound 3) in particular is very effective in this test.

Example 23

Stimulation of root growth in wheat and cotton

Compounds of formula I are employed in the form of aqueous dispersions prepared from a 25% wettable powder. The test is carried out with seeds which are sown in plastic boxes measuring 5×35×60 cm and filled with soil (15 seeds per box). The seeds are treated before sowing at rates of application of 45–500 mg per kg of seeds. The boxes are kept under controlled conditions in a climatic chamber. After 30 days, the plants are carefully washed with water to remove the soil and the length and dry weight of the roots are assessed.

Of the compounds of formula I, 2-nitro-5-(5'-trifluoromethyl-2'-pyridyloxy)phenylphosphonic acid (compound 3) in particular is every effective in this test.

TABLE 4

| mg a.i./kg of seeds | 45 | 150 | 500 |
|---|---|---|---|
| wheat: | | | |
| length expressed as % of controls | 98 | 107 | 107 |
| weight expressed as % of controls | 105 | 112 | 110 |
| cotton: | | | |
| length expressed as % controls | 122 | 111 | 122 |
| weight expressed as % of controls | 105 | 97 | 129 |

(controls = 100%)

Example 24

Action against Erysiphe graminis on barley

Barley plants about 8 cm in height are sprayed with a spray mixture (0.02% of compound of formula I) prepared from a 25% emulsifiable concentrate. After 3-4 hours the plants are dusted with conidia of Erysiphe graminis. The infected barley plants are then stood in a greenhouse at about 22° C. Evaluation of fungus attack is made 10 days later.

Of the compounds of formula I, dimethyl 2-nitro-5-(5'-trifluoromethyl-2'-pyridyloxy)phenylphosphonate (compound 1) is particularly effective in this test. Compared with untreated control plants (=100% attack), fungus attack is reduced by 80–95%.

Example 25

Action against mould fungus on moist maize

Dry maize grains (portions of 80 g each) are thoroughly mixed in sealable plastic beakers with an aqueous suspension prepared from a 25% wettable powder formulation of a compound of formula I. The application is so adjusted as to give a concentration of 0.06% of active ingredient, based on the weight of dry maize. A moistened slip of paper provides for a saturated humid atmosphere in the beakers which are filled with maize and then sealed. A mixed population of mould fungi develops spontaneously after incubation for 2–3 weeks at about 20° C. in the maize samples which have been treated only with water. The effectiveness of the test compounds is assessed by evaluating the degree of fungus development after 3 weeks.

Maize samples which are free from fungus attack or which exhibit only insignificant attack are incubated for a further 2 months. A visual assessment is made after each month according to the same criteria as specified above.

Of the compounds of formula I, 2-nitro-5-(5'-trifluoromethyl-2'-pyridyloxy)phenylphosphonic acid (compound 3) has a particularly pronounced fungicidal activity. Compared with untreated controls, fungus attack is reduced after 3 weeks by 80–95%, after a further month also by 80–95%, and after yet a further month still by 50–80%.

Example 26

Action against Xanthomonas oryzae in rice (Residual-protective action)

Three weeks after being reared in a greenhouse, rice plants of the variety "Caloro" or "S6" are sprayed at different concentrations with a spray mixture prepared from a 10% or 25% wettable powder formulation of a compound of formula I. The spray coating is left to dry for 1 day and the plants are then put into a climatic chamber at 24° and 75–85% relative humidity and infected by cutting off the tips of the leaves with scissors which have been dipped beforehand in a suspension of Xanthomonas oryzae. After incubation for 10 days in the same room, the cut leaves wither, roll up and become necrotic. The effectiveness of the test compounds is assessed by determining the extent of these symptoms.

Of the compounds of formula I, in particular dimethyl 2-nitro-5-(3'-chloro-5'-trifluoromethyl-2'-pyridyloxy)phenylphosphonate (compound 6) and dimethyl 2-nitro-5-(3',5'-dichloro-2'-pyridyloxy)phenylphosphonate (compound 4) exhibit pronounced bactericidal properties. An action of over 95% is achieved with compound 6 at a concentration of 0.02% and with compound 4 at a concentration of 0.006%. Compound 4 still has an action of 80–95% at a concentration of 0.0006%.

Example 27

Action against Xanthomonas oryzae on rice (systemic action)

Three weeks after being reared in a greenhouse, rice plants of the variety "Caloro" or "S6" are sprayed with a suspension prepared from a 25% wettable powder formulation of a compound of formula I (0.006% and 0.0006%, based on the volume of the soil). Three days after this treatment the plants are put into a climatic chamber at 24° C. and 75–85% relative humidity and infected by cutting off the tips of the leaves with scissors which have been dipped beforehand in a suspension of Xanthomonas oryzae. After incubation for 10 days in the same room, the cut leaves wither, roll up and become necrotic. The activity of the test compounds is assessed by determining the extent of these symptoms.

Of the compounds of formula I, dimethyl 2-nitro-5-(3',5'-dichloro-2'-pyridyloxy)phenylphosphonate (compound 4) in particular exhibits in this test a pronounced bactericidal activity: over 95% at a concentration of 0.006% and 50–80% at a concentration of 0.0006%.

Example 28

Postemergence herbicidal action (contact herbicide)

The plants for testing are sprayed postemergence (in the 4- to 6-leaf stage) at a concentration of 4 kg a.i./ha with an aqueous dispersion prepared from a compound of formula II formulated as a 25% wettable powder. The plants are then kept at 24°–26° C. and 45–60% relative humidity. The test is evaluated 15 days later according to the following rating:

| | |
|---|---|
| 1 = | plants completely withered |
| 2–3 = | very pronounced action |
| 4–6 = | medium action |
| 7–8 = | insignificant action |
| 9 = | no action (as untreated controls) |

Of the compounds of formula II, 1,2-dinitro-4-(3'-chloro-5'-trifluoromethyl-2'-pyridyloxy)benzene (compound II-2) and 1,2-dinitro-4-(5'-trifluoromethyl-2'-pyridyloxy)benzene (compound II-3) exhibit an excellent herbicidal action against Phaseolus and Solanum:

| Compound | Phaseolus | Solanum |
|---|---|---|
| II-2 | 1 | 1 |
| II-3 | 1 | 3 |

What is claimed is:

1. A compound of the formula I 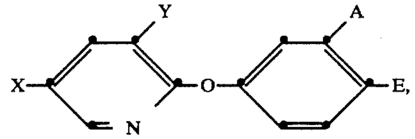 (I)

wherein X is halogen or trifluoromethyl, Y is hydrogen or halogen, one of the two substituents A and E is a phosphonate group 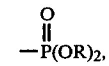 wherein R is $C_1$–$C_4$alkyl or hydrogen and the other is a nitro group, or a metal salt "selected from amongst alkali, alkaline earth and transition metals" thereof or a salt thereof with ammonium or an organic nitrogen base.

2. A compound according to claim 1, wherein X is chloride or trifluoromethyl, Y is hydrogen or chlorine, one of A and E is the phosphonate group wherein R is hydrogen, methyl or ethyl, and the other is the nitro group.

3. Dimethyl 2-nitro-5-(5'-trifluoromethyl-2'-pyridyloxy)phenylphosphonate according to claim 1.

4. 2-Nitro-5-(5'-trifluoromethyl-2'-pyridyloxy)-phenylphosphonic acid according to claim 1.

5. Dimethyl 2-nitro-5-(3',5'-dichloro-2'-pyridyloxy)-phenylphosphonate according to claim 1.

6. 2-Nitro-5-(3',5'-dichloro-2'-pyridyloxy)phenylphosphonic acid according to claim 1.

7. Dimethyl 2-nitro-5-(3'-chloro-5'-trifluoromethyl-2'-pyridyloxy)phenylphosphonate according to claim 1.

8. Diethyl 2-nitro-5-(3'-chloro-5'-trifluoromethyl-2'-pyridyloxy)phenylphosphonate according to claim 1.

9. 2-Nitro-5-(3'-chloro-5'-trifluoromethyl-2'-pyridyloxy)phenylphosphonic acid according to claim 1.

10. Diethyl 2-nitro-5-(3',5'-dichloro-2'-pyridyloxy)-phenylphosphonate according to claim 1.

11. Diethyl 2-nitro-5-(5'-trifluoromethyl-2'-pyridyloxy)phenylphosphonate according to claim 1.

12. Dimethyl 2-nitro-4-(5'-trifluoromethyl-2'-pyridyloxy)phenylphosphonate according to claim 2.

13. A composition for controlling weeds, which comprises compound according to claim 1 as active component and an inert carrier.

14. A composition according to claim 13, which contains dimethyl 2-nitro-5-(3'-chloro-5'-trifluoromethyl-2'-pyridyloxy)phenylphosphonate as active component.

15. A composition for regulating plant growth, which comprises a compound according to claim 1 as active component and an inert carrier.

16. A composition according to claim 15 for regulating the growth of leguminosae.

17. A composition according to claim 16 for regulating the growth of soya beans.

18. A composition according to claim 17, which contains dimethyl 2-nitro-5-(5'-trifluoromethyl-2'-pyridyloxy)phenylphosphonate as active component.

19. A composition according to claim 17, which contains 2-nitro-5-(5'-trifluoromethyl-2'-pyridyloxy)-phenylphosphonic acid as active component.

20. A composition according to claim 15 for stimulating the root growth of cultivated plants.

21. A composition according to claim 20 for stimulating the root growth of cereals.

22. A composition according to claim 21 for stimulating the root growth of wheat.

23. A composition according to claim 20 for stimulating the root growth of cotton plants.

24. A composition according to claim 20, which contains 2-nitro-5-(5'-trifluoromethyl-2'-pyridyloxy)phenylphosphonic acid as active component.

25. A composition according to claim 20, which contains 2-nitro-5-(3',5'-dichloro-2'-pyridyloxy)phenylphosphonic acid as active component.

26. A composition for controlling phytopathogenic fungi, which comprises a compound according to claim 1 as active component and an inert carrier.

27. A composition according to claim 26, which contains dimethyl 2-nitro-5-(5'-trifluoromethyl-2'-pyridyloxy)phenylphosphonate as active component.

28. A composition according to claim 26, which contains 2-nitro-5-(5'-trifluoromethyl-2'-pyridyloxy)phenylphosphonic acid as active component.

29. A composition for controlling phytopathogenic bacteria, which comprises a compound according to claim 1 as active component and an inert carrier.

30. A composition according to claim 29, which contains dimethyl 2-nitro-5-(3',5'-dichloro-2'-pyridyloxy)phenylphosphonate as active component.

31. A composition according to claim 29, which contains dimethyl 2-nitro-5-(3'-chloro-5'-trifluoromethyl-2'-pyridyloxy)phenylphosphonate as active component.

32. A method of controlling weeds, which comprises applying to said weeds, to parts thereof or to the locus thereof a herbicidally effective amount of a compound according to claim 1.

33. A method according to claim 32, wherein dimethyl 2-nitro-5-(3'-chloro-5'-trifluoromethyl-2'-pyridyloxy)phenylphosphonate is applied.

34. A method of regulating plant growth, which comprises applying to plants, to parts thereof or to the locus thereof, a growth regulating effective amount of a compound according to claim 1.

35. A method according for regulating the growth of cultivated plants, which comprises applying to said plants a growth regulating effective amount of a compound according to claim 1.

36. A method according to claim 35 for regulating the growth of leguminosae.

37. A method according to claim 36 for regulating the growth of soya beans.

38. A method according to claim 37, wherein dimethyl 2-nitro-5-(5'-trifluoromethyl-2'-pyridyloxy)phenylphosphonate is applied.

39. A method for stimulating the root growth of cultivated plants, which comprises applying to said plants a growth regulating effective amount of a compound according to claim 1.

40. A method according to claim 39 for stimulating the root growth of cereals.

41. A method according to claim 40 for stimulating the root growth of wheat.

42. A method according to claim 39 for stimulating the root growth of cotton plants.

43. A method according to claim 39, wherein 2-nitro-5-(5'-trifluoromethyl-2'-pyridyloxy)phenylphosphonic acid is applied.

44. A method according to claim 39, wherein 2-nitro-5-(3',5'-dichloro-2'-pyridyloxy)phenylphosphonic acid is applied.

45. A method of controlling phytopathogenic fungi, which comprises applying to plants or to parts thereof a fungicidally effective amount of a compound according to claim 1.

46. A method according to claim 45, wherein dimethyl 2-nitro-5-(5'-trifluoromethyl-2'-pyridyloxy)phenylphosphonate is applied.

47. A method according to claim 45, wherein 2-nitro-5-(5'-trifluoromethyl-2'-pyridyloxy)phenylphosphonic acid is applied.

48. A method of controlling phytopathogenic bacteria, which comprises applying to plants or to parts thereof a bactericidally effective amount of a compound according to claim 1.

49. A method according to claim 48, wherein dimethyl 2-nitro-5-(3',5'-dichloro-2'-pyridyloxy)phenylphosphonate is applied.

50. A method according to claim 48, wherein dimethyl 2-nitro-5-(3'-chloro-5'-trifluoromethyl-2'-pyridyloxy)phenylphosphonate is applied.

51. A compound according to claim 2, wherein A is the phosphonate group

and E is the nitro group.

52. A compound according to claim 51 wherein X is chlorine or trifluoromethyl and Y is hydrogen or chlorine.